United States Patent [19]

Estes

[11] Patent Number: 5,441,152

[45] Date of Patent: Aug. 15, 1995

[54] ORGANIZER DEVICES FOR ORTHOPEDIC EQUIPMENT NORMALLY FOUND IN CAST REMOVAL SITUATIONS

[76] Inventor: Ronald L. Estes, 25 Forest Pines Dr., Statesboro, Ga. 30458

[21] Appl. No.: 219,439

[22] Filed: Mar. 29, 1994

[51] Int. Cl.⁶ .................. B65D 69/00; B65D 1/34; B65D 6/04
[52] U.S. Cl. ................... 206/570; 206/562; 206/563; 206/564; 206/349; 206/363; 206/364; 206/370
[58] Field of Search ............... 206/363, 564, 570, 364, 206/370, 349, 562, 563

[56] References Cited

U.S. PATENT DOCUMENTS

| | | | |
|---|---|---|---|
| 3,371,975 | 3/1968 | Meltzer | 206/349 |
| 4,153,160 | 5/1979 | Leigh | 206/564 |
| 5,031,768 | 7/1991 | Fischer | 206/370 |
| 5,339,955 | 8/1994 | Horan et al. | 206/364 |

Primary Examiner—Steven N. Meyers
Assistant Examiner—Tara L. Laster

[57] ABSTRACT

An organizer device for orthopedic equipment normally found in cast removal situations comprising a plastic box with a closed lower surface, an opened upper surface and a peripheral wall therearound, the box being vacuum formed with recesses and projections therein, a central recess having a semi-cylindrical end formed into one peripheral wall for the receipt of the cord of a saw, the central recess having a semi-cylindrical central extent extending to a central extent of the container, and the central recess having enlarged projections extending upwardly from the end of the recess remote from the end recess for supporting the head of a saw; and a plurality of supplemental recesses formed on opposite sides of the central recess.

1 Claim, 3 Drawing Sheets

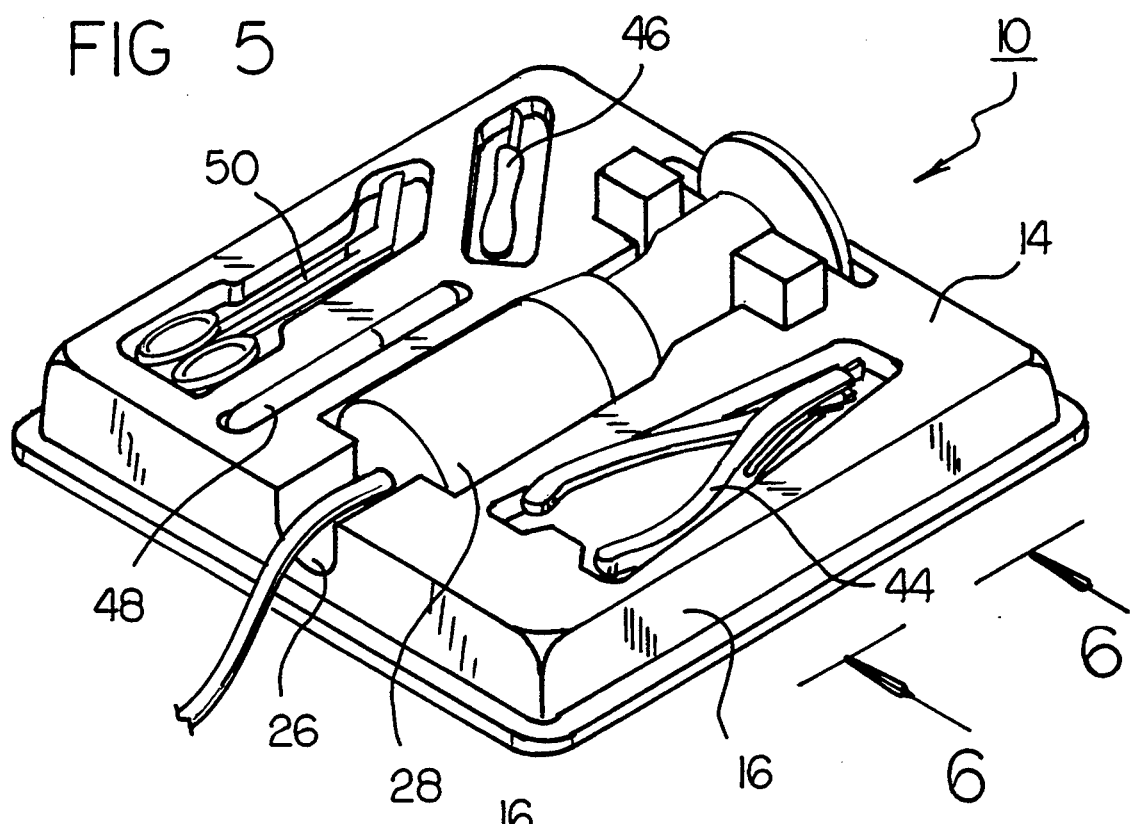
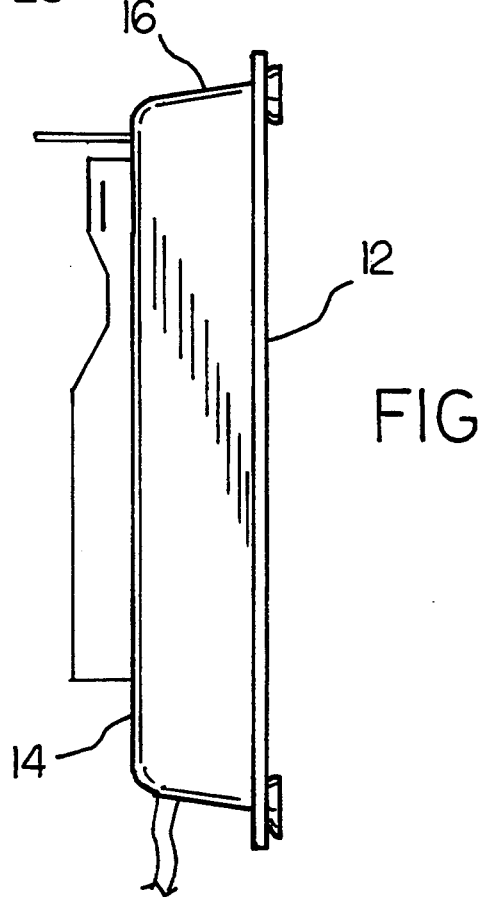

ORGANIZER DEVICES FOR ORTHOPEDIC EQUIPMENT NORMALLY FOUND IN CAST REMOVAL SITUATIONS

BACKGROUND OF THE INVENTION

1. Field of the Invention

The present invention relates to organizer device for orthopedic equipment normally found in cast removal situations and more particularly pertains to organizing and maintaining orthopedic surgical devices in a convenient manner.

2. Description of the Prior Art

The use of devices for storing surgical instruments is known in the prior art. More specifically, devices for storing surgical instruments heretofore devised and utilized for the purpose of storing miscellaneous instruments associated with surgery are known to consist basically of familiar, expected, and obvious structural configurations, notwithstanding the myriad of designs encompassed by the crowded prior art which has been developed for the fulfillment of countless objectives and requirements.

By way of example, the prior art discloses in U.S. Pat. No. 3,862,686 to Kolarik et al. a power saw utility case.

U.S. Pat. No. 4,341,304 to Diller discloses a simple tool tray.

U.S. Pat. No. 5,096,065 to Vigue discloses a molded tray for holding different size containers.

U.S. Pat. No. 5,114,108 to Olschansky discloses a detachable convenience food tray for vehicles.

U.S. Pat. No. Des. 297,167 to Steinman discloses the design of a medical equipment storage tray.

In this respect, the organizer device for orthopedic equipment normally found in cast removal situations according to the present invention substantially departs from the conventional concepts and designs of the prior art, and in doing so provides an apparatus primarily developed for the purpose of organizing and maintaining orthopedic surgical devices in a convenient manner.

Therefore, it can be appreciated that there exists a continuing need for new and improved organizer device for orthopedic equipment normally found in a cast removal situation which can be used for organizing and maintaining orthopedic surgical devices in a convenient manner. In this regard, the present invention substantially fulfills this need.

SUMMARY OF THE INVENTION

In view of the foregoing disadvantages inherent in the known types of devices for storing surgical instruments now present in the prior art, the present invention provides an improved organizer device for orthopedic equipment normally found in a cast removal situation. As such, the general purpose of the present invention, which will be described subsequently in greater detail, is to provide a new and improved organizer device for orthopedic equipment normally found in a cast removal situation and method which has all the advantages of the prior art and none of the disadvantages.

To attain this, the present invention essentially comprises a new and improved organizer device for orthopedic equipment normally found in a cast removal situation comprising: a plastic box with a closed lower surface, an opened upper surface and a peripheral wall therearound, the box being vacuum formed with recesses and projections therein, a central recess having a semi-cylindrical end formed into one peripheral wall for the receipt of the cord of a saw, the central recess having a semi-cylindrical central extent extending to a central extent of the container, and the central recess having enlarged projections extending upwardly from the end of the recess remote from the end recess for supporting the head of a saw; and a plurality of supplemental recesses formed on opposite sides of the central recess, the supplemental recesses being shaped to receive surgical instruments including a cast spreader, cast knife, scalpel, pen and bandage scissors.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent of legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide new and improved organizer devices for orthopedic equipment normally found in cast removal situations which have all the advantages of the prior art devices for storing surgical instruments and none of the disadvantages.

It is another object of the present invention to provide new and improved organizer devices for orthopedic equipment normally found in cast removal situations which may be easily and efficiently manufactured and marketed.

It is further object of the present invention to provide new and improved organizer device for orthopedic equipment normally found in a cast removal situation which are of durable and reliable constructions.

An even further object of the present invention is to provide new and improved organizer device for orthopedic equipment normally found in a cast removal situation which are susceptible of a low cost of manufacture with regard to both materials and labor, and which accordingly are then susceptible of low prices of sale to the consuming public, thereby making such organizer device for orthopedic equipment normally found in a cast removal situation economically available to the buying public.

Still yet another object of the present invention is to provide new and improved organizer device for orthopedic equipment normally found in a cast removal situation which provide in the apparatuses and methods of the prior art some of the advantages thereof, while simultaneously overcoming some of the disadvantages normally associated therewith.

Still another object of the present invention is to organize and maintain orthopedic surgical devices in a convenient manner.

Lastly, it is an object of the present invention to provide new and improved organizer device for orthopedic equipment normally found in a cast removal situation comprising: a plastic box with a closed lower surface, an opened upper surface and a peripheral wall therearound, the box being vacuum formed with recesses and projections therein, a central recess having a semi-cylindrical end formed into one peripheral wall for the receipt of the cord of a saw. The central recess having a semi-cylindrical central extent extending to a central extent of the container, and the central recess having enlarged projections extending upwardly from the end of the recess remote from the end recess for supporting the head of a saw; and a plurality of supplemental recesses formed on opposite sides of the central recess.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 5 is an enlarged showing of the device of the prior Figures but illustrating surgical instruments stored therein.

FIG. 6 is a side elevational view taken along lines 6—6 of FIG. 5.

The same reference numerals refer to the same parts through the various Figures.

DESCRIPTION OF THE PREFERRED EMBODIMENT

Figure 1:
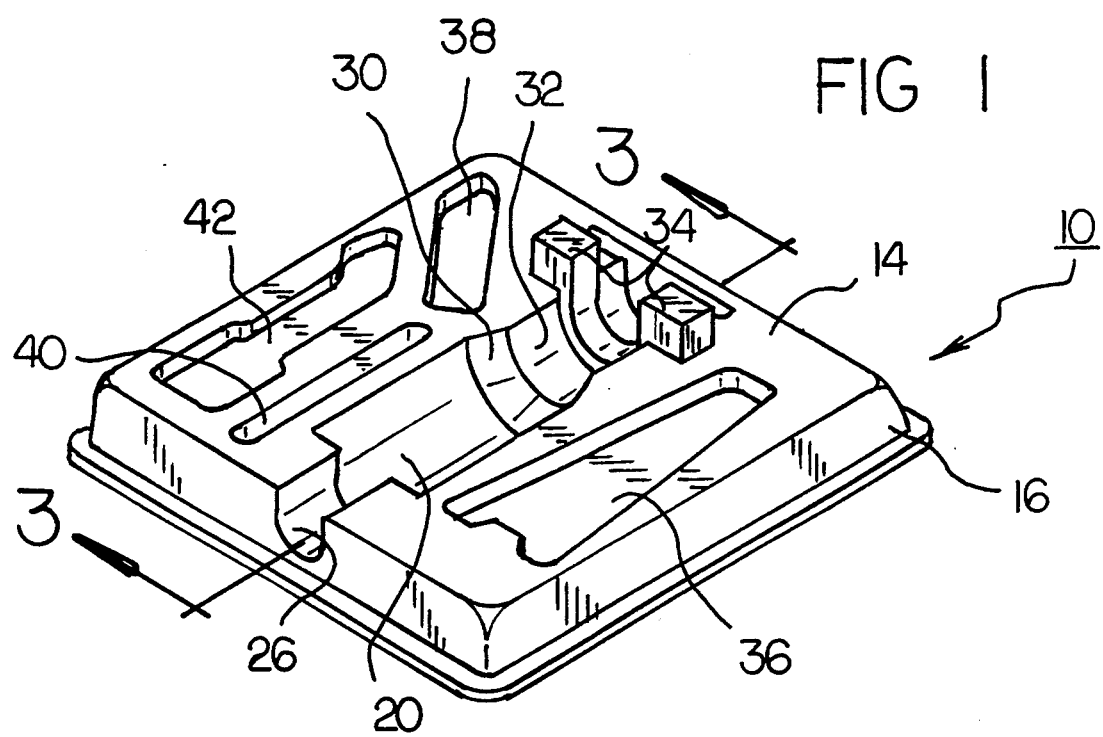
FIG. 1 is a perspective view of the preferred embodiment of new and improved the organizer device for orthopedic equipment normally found in a cast removal situation constructed in accordance with the principles of the present invention.
Figure 2:
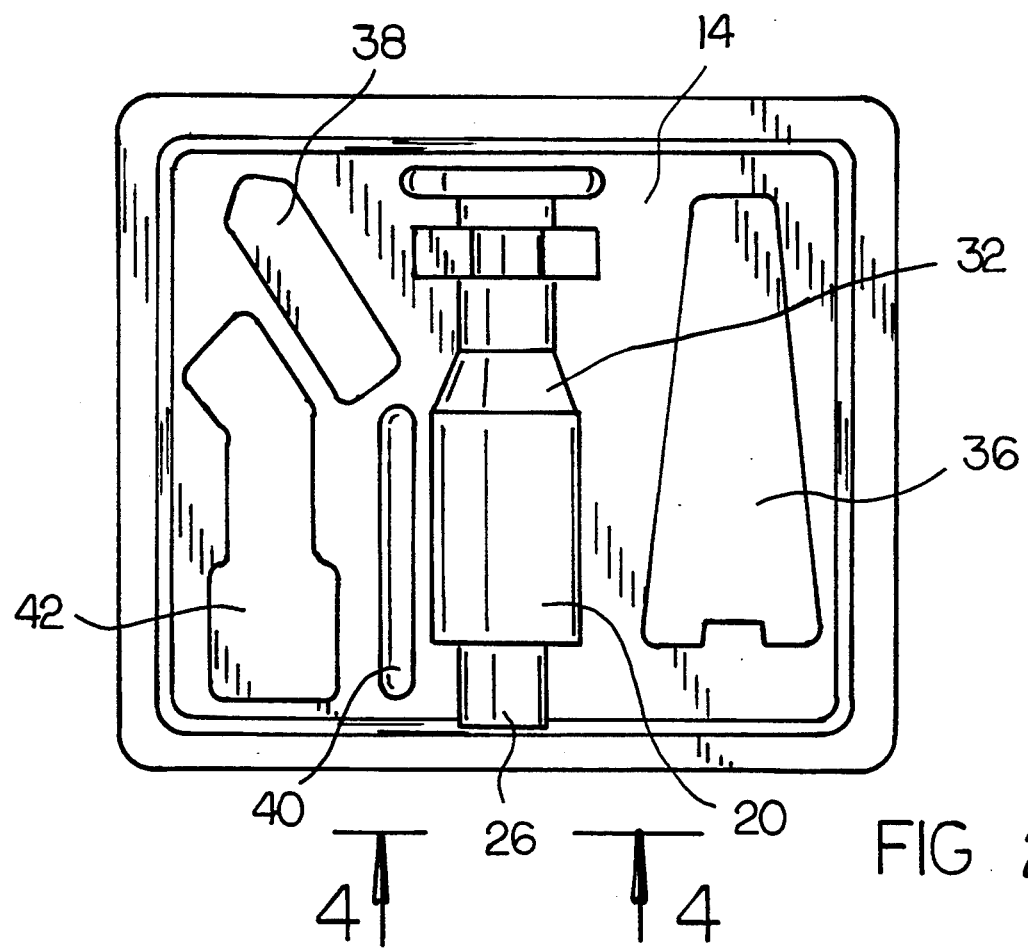
FIG. 2 is a plan view of the device shown in the prior Figures.
Figure 3:
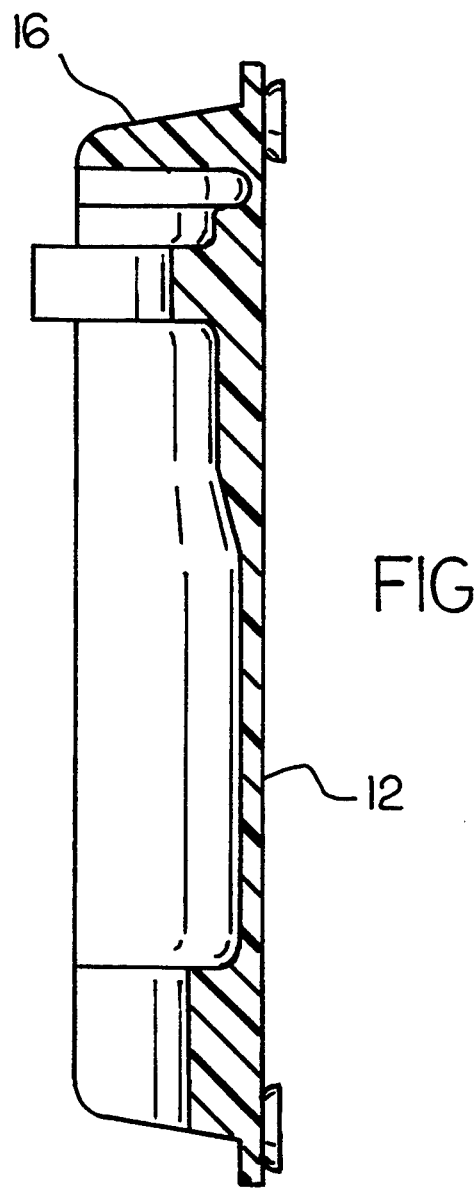
FIG. 3 is a cross-sectional view of the device taken along line 3—3 of FIG. 1.
Figure 4:
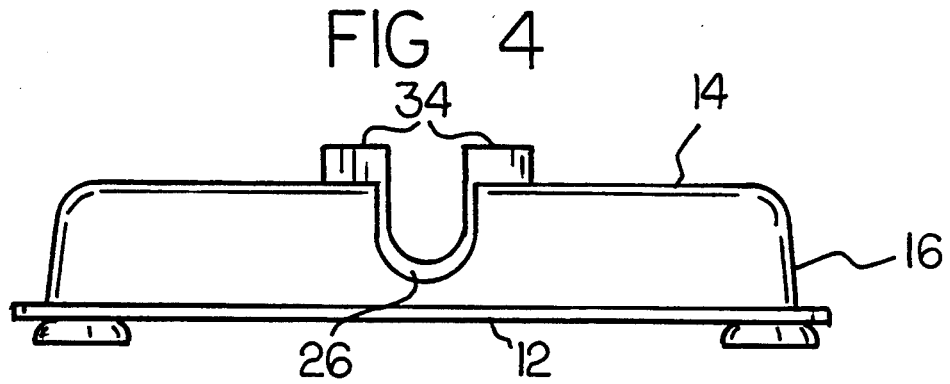
FIG. 4 is an elevational view of the device shown in the prior Figures.

With reference now to the drawings, and in particular to FIG. 1 thereof, the preferred embodiment of the new and improved organizer device for orthopedic equipment normally found in cast removal situations embodying the principles and concepts of the present invention and generally designated by the reference numeral 10 will be described.

Specifically, it will be noted in the various Figures that there is shown a new and improved organizer device for orthopedic equipment normally found in cast removal situations. The invention is a system 10 comprised of a plurality of components. Such components, in their simplest terms include a plastic box with a central recess, a plurality of supplemental recesses, and a peripheral wall. Such components are individually configured and correlated one to another so as to attain the deserved objectives.

More specifically, the plastic box is formed as a one-piece unit with a closed lower surface 12 and an upper open surface 14. The box also has a raised peripheral wall 16 therearound. The peripheral wall extends to a greater height than the remainder of the box therewithin. The box is preferably vacuum formed with recesses extending downwardly and projections extending upwardly.

The main or central recess 20 has a semi-cylindrical end recess 26 formed into one adjacent peripheral wall. Such end is for the receipt of the cord of a cast saw 28 to be positioned therein. The central recess 20 also has a conical region 30 extending to a central extent of the container. The central recess also has enlarged projections extending upwardly above the peripheral wall 16. Such projections extend upwardly from the end of the recess which is remote from the end recess 26 in the peripheral wall. The upstanding projections 34 are for supporting the head and blade of the cast saw.

Also provided in the box are a plurality of supplemental recesses 36, 38, 40, and 42. Such supplemental recesses are formed on opposite sides of the central recess. The supplemental recesses are various sizes and shapes and extend downwardly into the upper surface of the box. They are for receiving supplemental surgical instruments including a cast spreader 44, a cast knife 46, a pen 48, and bandage scissors 50.

Orthopedic surgeons typically use a cast saw, cast spreader, cast knife or scalpel, and bandage scissors when removing plaster casts from patients. These items are usually stored in different places, and must be collected and placed close together in an accessible location next to the patient before use. The present invention provides a convenient way for storing them, both when being used and when not in use.

The present invention is a clean, smooth, professional looking orthopedic instrument holding tray that has individual recessed pockets for each of the four cast removal instruments. It is designed to be placed on a bench, table, or counter top next to the patient, organizing and positioning the instruments where the user can quickly and easily access them. The recessed pockets hold the instruments safely and securely, help preventing accidents by shielding their sharp edges and points, and protect the counter top from cuts and scratches.

The present invention is made from thermal molded plastic. It measures 12 inches wide, 15 inches deep and 4 inches high. It has a flanged bottom edge and sloping, rounded sides for strength. The recessed pockets also have sloping sides with rounded corners for ease in cleaning. Nonskid pads are attached underneath each corner for security.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A new and improved organizer device for orthopedic equipment comprising:
   orthopedic equipment including a saw of the type having a head and a blade at one end and a power cord at the opposite end and, the orthopedic equipment also including a cast spreader, a cast knife, a pen and bandage scissors;
   a plastic box with a lower surface, and opened upper surface and a raised peripheral wall therearound, the box being vacuum formed with recesses and projections therein, the recesses including a central recess for the receipt of the saw with a semi-cylindrical end recess formed into one peripheral wall formed as an extension of the central recess for the receipt of the cord of a saw, the central recess having a conical central region extending to a central region of the box, and the central recess also having enlarged projections extending upwardly above the raised peripheral wall from the end of the recess remote from the end recess adapted to receive and support the head and blade of a saw; and
   a plurality of supplemental recesses formed on opposite sides of the central recess, the supplemental recesses being shaped to receive the surgical instruments including a cast spreader, a cast knife, a pen and bandage scissors.

* * * * *